United States Patent
Li et al.

(10) Patent No.: US 7,615,644 B2
(45) Date of Patent: Nov. 10, 2009

(54) USE OF IONIC LIQUIDS AS COORDINATION LIGANDS FOR ORGANOMETALLIC CATALYSTS

(75) Inventors: Zaiwei Li, Moreno Valley, CA (US); Yongchun Tang, Walnut, CA (US); Jihong Cheng, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 309 days.

(21) Appl. No.: 11/228,788

(22) Filed: Sep. 16, 2005

(65) Prior Publication Data

US 2006/0069169 A1 Mar. 30, 2006

Related U.S. Application Data

(60) Provisional application No. 60/610,835, filed on Sep. 17, 2004, provisional application No. 60/673,705, filed on Apr. 21, 2005.

(51) Int. Cl.
*C07D 233/54* (2006.01)
*C07C 27/00* (2006.01)

(52) U.S. Cl. .................................... 548/335.1; 568/910

(58) Field of Classification Search .............. 548/335.1; 568/910

See application file for complete search history.

(56) References Cited

U.S. PATENT DOCUMENTS

2004/0035293 A1  2/2004  Davis, Jr.

FOREIGN PATENT DOCUMENTS

| WO | WO 95/21806 | 8/1995 |
|----|-------------|--------|
| WO | WO 95/21871 | 8/1995 |
| WO | WO 95/21872 | 8/1995 |

OTHER PUBLICATIONS

Periana et al. "Platinum Catalysts for the High-Yield Oxidation of Methane to a Methanol Derivative" Science, 1998, vol. 280, pp. 560-564.*
Periana, R.A. et al., A Mercury-Catalyzed, High-Yield System for the Oxidation of Methane to Methanol, Science 259:340-343 (1993).
Periana, R.A. et al., Platinum Catalysts for the High-Yield Oxidation of Methane to a Methanol Derivative, Science 280:560-564 (1998).
Zhao, D. et al., Ionic Liquids: Applications in Catalysis, Catalysis Today 74:157:189 (2002).

* cited by examiner

*Primary Examiner*—Rebecca L Anderson
*Assistant Examiner*—Joseph R Kosack
(74) *Attorney, Agent, or Firm*—Seth D. Levy; Davis Wright Tremaine LLP

(57) ABSTRACT

Aspects of the present invention relate to compositions and methods for the use of ionic liquids with dissolved metal compounds as catalysts for a variety of chemical reactions. Ionic liquids are salts that generally are liquids at room temperature, and are capable of dissolving a many types of compounds that are relatively insoluble in aqueous or organic solvent systems. Specifically, ionic liquids may dissolve metal compounds to produce homogeneous and heterogeneous organometallic catalysts. One industrially-important chemical reaction that may be catalyzed by metal-containing ionic liquid catalysts is the conversion of methane to methanol.

19 Claims, 12 Drawing Sheets

USE OF IONIC LIQUIDS AS COORDINATION LIGANDS FOR ORGANOMETALLIC CATALYSTS

This application claims the benefit of priority from U.S. Provisional Application Ser. No. 60/610,835, filed Sep. 17, 2004 and U.S. Provisional Application Ser. No. 60/673,705, filed Apr. 21, 2005.

GOVERNMENT RIGHTS

The U.S. Government has certain rights in this invention pursuant to Grant No. DE-FC36-04GO14276 S-107,807 awarded by the Department of Energy.

FIELD OF THE INVENTION

The invention relates to compositions and methods involving ionic liquids and dissolved metal compounds as homogeneous and heterogeneous catalysts useful for catalyzing various chemical reactions.

BACKGROUND

Alkanes comprise a significant fraction of the world's petroleum and natural gas resources and have the potential to be a useful source of carbon for large-scale synthesis. Methane, the smallest alkane and the principal component of natural gas, is an abundant and inexpensive natural resource. Despite these attributes, it is typically only used as a fuel for power generation. The reason for methane's under utilization is that there are few commercially viable methods for converting methane to a product that is chemically-useful due to the strength of its covalent carbon-hydrogen (C—H) bonds, which are among the strongest of all hydrocarbons. The search for catalysts that can facilitate C—H bond activation in methane and other low molecular-weight alkanes is an area of research with considerable industrial significance.

The most common chemical use of methane is to convert it (by an indirect oxidation process) to methanol, a commercially important alcohol that is one of the top 25 chemicals produced worldwide. The conversion is generally carried out at high temperatures and pressures in a two-stage steam reforming process to form synthesis gas (carbon monoxide and hydrogen), and is coupled with a methanol synthesis process that dates back to the 1920s. The process is expensive, energy intensive, and impractical for use in the remote locations where many of the methane reserves are found. As a result, the direct oxidative conversion of methane to an easily transportable liquid such as methanol has been extensively investigated for decades.

Although various parties have been seeking simpler, more efficient methods for converting methane to methanol, no such methods have been commercialized due to the difficulty in finding a sufficiently active and selective catalyst. Although low temperature selective methane oxidation by transition metal complexes in solution has been the focus of substantial effort since the 1970s, the most promising catalysts so far described by Periana et al. 1993 and 1998 (Periana R. A., et al. (1993) *Science* 259:340, Periana R. A. et al., (1998) *Science* 280:560-564) have not yet been commercialized. The process described by Periana et al. in 1998 utilizes a platinum bipyrimidine catalyst and requires concentrated sulfuric acid. This catalyst converts the methane to methyl bisulfate ($CH_3OSO_3H$), which can then be converted to methanol.

Ionic liquids are salts consisting of ions that exist in the liquid state at ambient temperatures, or salts that have melting points below around 300° C. Ionic liquids typically consist of organic nitrogen-containing heterocyclic cations and inorganic anions. Ionic liquids offer numerous advantages over conventional organic solvents for carrying out organic reactions, including very low vapor pressure, lack of flammability, and the capacity to be functionalized to suit particular reactions. Unlike conventional molten salts (for example, molten sodium chloride), ionic liquids often melt below 300° C. Since the melting points are low, ionic liquids can act as solvents in which reactions can be performed, and because the liquid is made of ions rather than molecules, such reactions often provide distinct selectivities and reactivities as compared to conventional organic solvents. In addition, their non-volatility results in low impact on the environment and human health, and they are recognized as solvents for "green" chemistry.

Ionic liquids have been disclosed for use as solvents for a broad spectrum of chemical processes. These ionic liquids, which in some cases can serve as both catalyst and solvent, are attracting increasing interest from industry because they promise significant environmental benefits. Several patent applications, including international PCT publication Nos. WO 95/21871, WO 95/21872, and WO 95/21806 relate to ionic liquids and their use to catalyze hydrocarbon conversion reactions such as polymerization and alkylation reactions.

There is a significant need in the art for readily available hydrocarbon sources that require a less expensive plant, which is cheaper to run, uses less energy, and produces fewer pollutants than the current technology. Ionic liquids may provide a new approach for facilitating this difficult yet important chemical reaction.

SUMMARY OF THE INVENTION

The invention disclosed herein relates to composition and methods useful for producing organometallic catalysts comprising ionic liquids and metal compounds. Embodiments of the invention provide for methods of facilitating a homogeneous or heterogeneous catalytic reaction, comprising providing a quantity of an ionic liquid and a quantity of a metal compound, contacting the metal compound with the ionic liquid such that at least a portion of the metal compound dissolves in the ionic liquid to produce an ionic liquid catalyst, and using the ionic liquid catalyst to facilitate a homogeneous or heterogeneous catalytic reaction.

Further embodiments relate to methods wherein the ionic liquid further comprises one or more cationic components and one or more anionic components.

Other embodiments relate to methods wherein the cationic component is selected from the group consisting of imidazolium-based cations, pyridinium-based cations, ammonium-based cations, phosphonium-based cations, thiazolium-based cations, triazolium-based cations, oxazolium-based cations, pyrazinium-based cations, pyrazolium-based cations, and combinations thereof, and further embodiments relate to methods wherein the cationic component is selected from the group consisting of imidizolium, 1-methylimidizolium, 1,3-dimethylimidizolium, and combinations thereof.

Some embodiments of the invention relate to methods wherein the anionic component is selected from the group consisting of chloride, bromide, iodide, bisulfate, triflate, trifluoroacetate, methanesulfate, and combinations thereof.

Additional embodiments relate to methods wherein the ionic liquid is selected from the group consisting of 1-methylimidazolium chloride, 1-methylimidazolium bisulfate, 1-methylimidazolium triflate, imidazolium chloride, imidazolium bisulfate, 1,3-dimethylimidazolium iodide, 1,3-dimethylimidazolium bisulfate, and combinations thereof.

Further embodiments relate to methods wherein the ionic liquid has a melting point between about −100° C. and about 300° C., and still further embodiments relate to methods wherein the ionic liquid has a melting point between about 30° C. and 300° C.

Certain embodiments relate to methods wherein the metal compound comprises a metal selected from the group consisting of main group metals, transition metals, and combinations thereof, and further embodiments relate to methods wherein the metal compound comprises a metal selected from the group consisting of platinum, palladium, iridium, rhodium, ruthenium, rhenium, gold, silver, mercury, chromium, molybdenum, tungsten, titanium, zirconium, iron, manganese, technetium, osmium, copper, vanadium, niobium, tantalum, and cobalt.

Still further embodiments relate to methods wherein the metal compound is selected from the group consisting of $PtCl_2$, $PtC_4$, $PtO_2$, and combinations thereof.

Other embodiments relate to methods wherein the molar ratio of the amount of ionic liquid to the amount of the metal compound is from about 1,000,000:1 to about 1:1.

Embodiments of the invention described herein provide for ionic liquid catalysts that comprise an ionic liquid and a metal compound, or a combination thereof. Further embodiments comprise ionic liquid catalysts wherein the ionic liquid further comprises one or more cationic components and one or more anionic components.

Further embodiments relate to ionic liquid catalysts wherein the cationic component is selected from the group consisting of imidizolium-based cations, pyridinium-based cations, ammonium-based cations, phosphonium-based cations, thiazolium-based cations, triazolium-based cations, oxazolium-based cations, pyrazinium-based cations, pyrazolium-based cations, and combinations thereof.

Still further embodiments of the present invention relate to ionic liquid catalysts wherein the cationic component is selected from the group consisting of imidizolium, 1-methylimidizolium, 1,3-dimethylimidizolium, and combinations thereof.

Other embodiments of the present invention provide for ionic liquid catalysts wherein the anionic component is selected from the group consisting of chloride, bromide, iodide, bisulfate, triflate, trifluoroacetate, methanesulfate, and combinations thereof.

Additional embodiments of the present invention provide ionic liquid catalysts wherein the ionic liquid is selected from the group consisting of 1-methylimidazolium chloride, 1-methylimidazolium bisulfate, 1-methylimidazolium triflate, imidazolium chloride, imidazolium bisulfate, 1,3-dimethylimidazolium iodide, 1,3-dimethylimidazolium bisulfate, and combinations thereof.

Further embodiments relate to ionic liquid catalysts wherein the ionic liquid has a melting point between about −100° C. and about 300° C., and still further embodiments relate to methods wherein the ionic liquid has a melting point between about 30° C. and 300° C.

Other embodiments of the invention include ionic liquid catalysts wherein the metal compound comprises metals selected from the group consisting of main group metals, transition metals, and combinations thereof, including platinum, palladium, iridium, rhodium, ruthenium, rhenium, gold, silver, mercury, chromium, molybdenum, tungsten, titanium, zirconium, iron, manganese, technetium, osmium, copper, vanadium, niobium, tantalum, and cobalt. Further embodiments provide for ionic liquid catalysts wherein the metal compound is $PtCl_2$, $PtCl_4$, $PtO_2$, or combinations thereof.

Alternative embodiments of the invention provide for ionic liquid catalysts wherein the molar ratio of the amount of ionic liquid to the amount of the metal compound is from about 1,000,000:1 to about 1:1.

Embodiments of the present invention also provide a method for converting methane into an oxidized product, comprising contacting methane gas with an ionic liquid catalyst in the presence of sulfuric acid, and further provides methods wherein the ionic liquid catalyst comprises an ionic liquid and a metal compound.

Further embodiments of the invention provide methods wherein the ionic liquid is selected from the group consisting of 1-methylimidazolium chloride, 1-methylimidazolium bisulfate, 1-methylimidazolium triflate, imidazolium chloride, imidazolium bisulfate, 1,3-dimethylimidazolium iodide, 1,3-dimethylimidazolium bisulfate, and combinations thereof.

Still further embodiments of the invention provide for methods wherein the metal compound is selected from the group consisting of $PtCl_2$, $PtCl_4$, $PtO_2$, and combinations thereof.

Other embodiments provide methods wherein the contacting of the methane to the ionic liquid catalyst is by bubbling methane through the ionic liquid catalyst, or by pressurizing a reaction system with methane.

Additional embodiments relate to methods wherein the molar ratio of the amount of ionic liquid to the amount of metal compound is from about 1,000,000:1 to 1:1, and wherein the oxidized product is methylbisulfate.

Other embodiments relate to methods for producing methanol from methane gas comprising contacting methane gas with an ionic liquid catalyst in the presence of sulfuric acid.

Alternative embodiments provide for compositions comprising a quantity of methanol, produced by a process comprising providing an ionic liquid catalyst comprising an ionic liquid and a metal compound, contacting a quantity of methane with a quantity of the ionic liquid catalyst sufficient to convert at least a portion of the quantity methane to methylbisulfate, converting at least a portion of the methylbisulfate to methanol, and recovering at least a portion of the methanol.

BRIEF DESCRIPTION OF THE DRAWINGS

FIG. 1a shows an ammonium ion. FIG. 1b shows a sulfonium ion. FIG. 1c shows a phosphonium ion. FIG. 1d shows a lithium ion. FIG. 1e shows an imidazolium ion. FIG. 1f shows a pyridinium ion. FIG. 1g shows a picolinium ion. FIG. 1h shows a thiazolium ion. FIG. 1i shows a triazolium ion. FIG. 1j shows an oxazolium ion. FIG. 1k shows a pyrazolium ion.

FIG. 2a shows Pt(II) in [bmim] [Cl]; FIG. 2b shows Pt(IV) in [bmim] [Cl] if oxidized; FIG. 2c shows the product of FIG. 2a in $H_2SO_4$; FIG. 2d shows the product of FIG. 2b in $H_2SO_4$.

FIG. 3 shows $^1H$ NMR spectra of the liquid of $H_2SO_4$/[bpym]$PtCl_2$/[bmim][Cl] ternary system after rate tests using the low pressure reactor, in accordance with an embodiment of the present invention.

FIG. 4 shows $^1$H NMR spectra of the liquid of $H_2SO_4$/Catalyst/$CH_4$ ternary system after methane oxidation tests using the high pressure reactor in accordance with an embodiment of the present invention.

FIG. 6a shows a $PtCl_4$+ IL-003 system; FIG. 6b shows a $PtO_2$+IL006 system. Acetic acid was used as the internal standard.

DETAILED DESCRIPTION OF THE INVENTION

Figure 1:
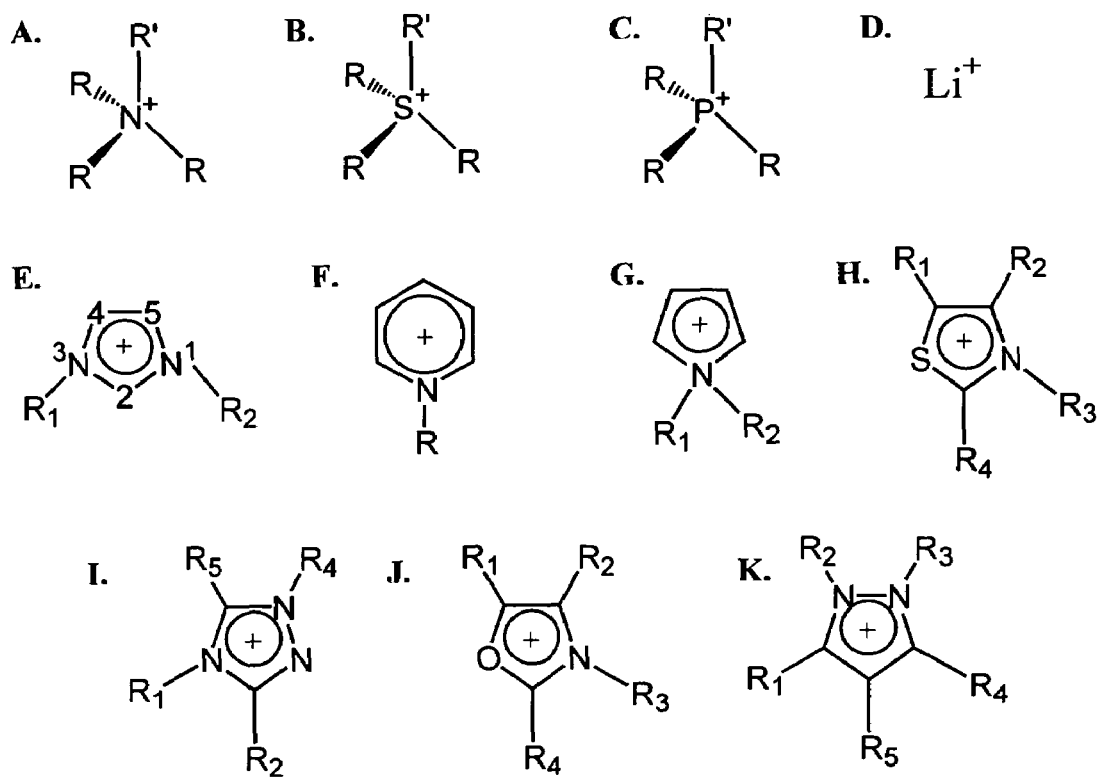
FIG. 1 shows examples of cationic components of ionic liquids in accordance with certain embodiments of the present invention.

The invention disclosed herein generally relates to the use of ionic liquids to dissolve metal compounds to produce organometallic catalyst solutions. Such organometallic catalyst solutions can be used to efficiently promote a number of chemical reactions, including reactions involving the activation of a carbon-hydrogen (C—H) bond, such as the oxidation of methane and the alkylation of organic compounds. The compositions and methods described herein improve upon the platinum-based catalyst system described by Periana et al. (Periana R. A. et al., (1998) *Science* 280:560-564).

DEFINITIONS

As used herein, the term "catalyst" is a substance that accelerates the rate of a chemical reaction at some temperature. A catalyst generally participates in the reaction but is neither a chemical reactant nor a chemical product.

The term "reactant" refers to a chemical substance that is present at the start of a chemical reaction.

The term "oxidation" refers to a chemical reaction that involves a loss of one or more electrons by one molecule. Oxidations often result the addition of oxygen to a compound that accompanies a loss of electrons.

A "homogeneous catalyst" is a substance that accelerates the rate of a chemical reaction in a system wherein the catalyst is in the same phase as the reaction medium. An example of a homogeneous catalytic system is one in which the catalyst is a liquid and the reaction medium is a liquid, or a system in which the catalyst is a solid that is dissolved in the reaction medium forming a homogeneous solution. It is also possible that the reaction medium itself be a component of the catalytic system. A homogeneous catalytic reaction is a reaction in which the catalyst, reactants, and reaction medium are in the same phase.

A "heterogeneous catalyst" is a substance that accelerates the rate of a chemical reaction wherein one or more of the catalysts are in a different phase than the reaction medium. For example, a solid metal catalyst may be used to in a liquid-phase reaction system. Another example of a heterogeneous catalytic solution is a slurry, wherein one or more of the catalysts exist in a solid phase. In situations involving a metal catalyst in a liquid reaction medium, the rate of transport of reactants and products to and from the solid catalytic surface may limit the overall rate of the reaction due to the inherent limitation of surface area. As a result, homogeneous catalytic systems are generally more efficient than heterogeneous catalytic systems. A heterogeneous catalytic reaction is a reaction in which the catalyst, reactants, and reaction medium exist in more than one phase.

An "ionic liquid" is defined herein as a salt that has a melting point between around −100° C. and around 300° C. Ionic liquids comprise one or more cations or cationic components, and one or more anions or anionic components. In some cases, the cations or anions may be related species in equilibrium. Many ionic liquids have been disclosed in the literature as well as in patents and patent applications. Published U.S. Patent Application 2004/0035293A1 as well as Dongbin et al. (Dongbin, Z et al., (2002) *Catalysis Today* 74:157-189) disclose a number of ionic liquids. In addition, Table 1 shows a number of ionic liquid compounds that have been synthesized by the inventors, but are by no means intended to limit the scope of the present invention.

TABLE 1

List of ionic liquids that may be used to produce ionic liquid catalysts.

| IL No. | Name | Abbreviation |
|---|---|---|
| IL-001 | 1-neopentyl-3-methylimidazolium chloride | [npmim][Cl] |
| IL-002 | 1-isopropyl-3-methylimidazolium bromide | [ipmim][Br] |
| IL-003 | 1-methylimidazolium chloride | [1-mim][Cl] |
| IL-004 | 1-methylimidazolium bisulfate | [1-mim][$HSO_4$] |
| IL-005 | 1-methylimidazolium triflate | [1-mim][$CF_3SO_4$] |
| IL-006 | Imidazolium chloride | [im][Cl] |
| IL-007 | Imidazolium bisulfate | [im][$HSO_4$] |
| IL-008 | 1,3-dimethylimidazolium iodide | [mmim][I] |
| IL-009 | 1,3-dimethylimidazolium bisulfate | [mmim][$HSO_4$] |
| IL-010 | Tetramethylammonium trifluoroacetate | |
| IL-011 | 2-methylimidazolium bisulfate | [2-mim][$HSO_4$] |
| IL-012 | 4-methylimidazolium bisulfate | [4-mim][$HSO_4$] |
| IL-013 | 1,2-dimethylimidazolium bisulfate | [1,2-dimim][$HSO_4$] |
| IL-014 | 1,4-dimethylimidazolium bisulfate | [1,4-dimim][$HSO_4$] |
| IL-015 | 1,2,3-trimethylimidazolium methanesulfate, | [1,2,3-trimim][$CH_3SO_4$] |
| IL-016 | 2,4,5-trimethyloxazolium bisulfate | [2,4,5-trimox][$HSO_4$] |
| IL-017 | 1-trifluoroacetylimidazolium bisulfate | |
| IL-018 | 1-methylbenzimidazolium bisulfate | |
| IL-019 | 1,3-dimethylbenzimidazolium bisulfate | |
| IL-020 | Pyridinium bisulfate | [pyr][$HSO_4$] |
| IL-021 | 1,4-dimethylpyridinium bisulfate | |
| IL-022 | 2,6-lutidinium bisulfate | |
| IL-023 | 3,5-lutidinium bisulfate | |
| IL-024 | Pyrazinium bisulfate | [pyz][$HSO_4$] |
| IL-025 | 1-methylpyrazinium bisulfate | |
| IL-026 | 2-methylpyrazinium bisulfate | |
| IL-027 | 2,3-dimethylpyrazinium bisulfate | |
| IL-028 | 2,3,5-trimethylpyrazinium bisulfate | |
| IL-029 | 2,3,5,6-tetramethylpyrazinium bisulfate | |
| IL-030 | 1,2,3,5,6-pentamethylpyrazinium bisulfate | |
| IL-031 | Quinoxalinium bisulfate | |
| IL-032 | Quinoxalinium chloride | |

TABLE 1-continued

List of ionic liquids that may be used to produce ionic liquid catalysts.

| IL No. | Name | Abbreviation |
|---|---|---|
| IL-033 | Pyrimidinium bisulfate | |
| IL-034 | 1-methylpyrimidinium bisulfate | |
| IL-035 | 4,6-dimethylpyrimidinium bisulfate | |
| IL-036 | Triazinium bisulfate | |
| IL-037 | Bipyrimidinium bisulfate | |
| IL-038 | 1-methylbipyrimidinium bisulfate | |

A "cation" is defined as a positively-charged atom, molecule or compound. Examples of cationic components of ionic liquids include but are not limited to 1-neopentyl-3-methylimidazolium, 1-isopropyl-3-methylimidazolium, 1-methylimidazolium, imidazolium, 1,3-dimethylimidazolium, tetramethylammonium, 2-methylimidazolium, 4-methylimidazolium, 1,2-dimethylimidazolium, 1,4-dimethylimidazolium, 1,2,3-trimethylimidazolium, 2,4,5-trimethyloxazolium, 1-trifluoroacetylimidazolium, 1-methylbenzimidazolium, 1,3-dimethylbenzimidazolium, pyridinium, 1,4-dimethylpyridinium, 2,6-lutidinium, 3,5-lutidinium, pyrazinium, 1-methylpyrazinium, 2-methylpyrazinium, 2,3-dimethylpyrazinium, 2,3,5-trimethylpyrazinium, 2,3,5,6-tetramethylpyrazinium, 1,2,3,5,6-pentamethylpyrazinium, quinoxalinium, pyrimidinium, 4,6-dimethylpyrimidinium, bipyrimidinium, and 1-methylbipyrimidinium. FIG. 1 shows the chemical structures of some of the ionic liquid cations.

"Imidizolium-based cations" are cations wherein the cation contains an imidizolium group, which may be substituted. "Pyridinium-based cations" are cations wherein the cation contains a pyridinium group, which may be substituted. "Ammonium-based cations" are cations wherein the cation contains an ammonium group, which may be substituted. "Phosphonium-based cations" are cations wherein the cation contains a phosphonium group, which may be substituted. "Thiazolium-based cations" are cations wherein the cation contains a thiazolium group, which may be substituted. "Triazolium-based cations" are cations wherein the cation contains a triazolium group, which may be substituted. "Oxazolium-based cations" are cations wherein the cation contains an oxazolium group, which may be substituted. "Pyrazolium-based cations" are cations wherein the cation contains a pyrazolium group, which may be substituted. "Pyrazinium-based cations" are cations wherein the cation contains a pyrazinium group, which may be substituted.

The term "anion" refers to a negatively-charged atom, molecule, or compound. Examples of ionic liquid anions that may be used in the reaction system disclosed herein include, but are not limited to, chloride (Cl$^-$), bromide (Br$^-$), iodide (I$^-$), bisulfate, (HSO$_4^-$), triflate (CF$_3$SO$_3^-$), tetrafluoroborate (BF$_4^-$), and methylsulfate (CH$_3$SO$_4^-$).

The term "organometallic" refers to an organic compound containing metal atoms.

As used herein, the term "ionic liquid catalyst" refers to an ionic liquid that has a metal compound dissolved in it. Ionic liquid catalysts may be either homogeneous or heterogeneous solutions.

The term "metal compound" refers to compounds that comprise one or more metals. Metals in metal compounds may be either free metal ions, solvated metal ions in a coordinated complex form, which may have one or more replaceable ligands, alloys of metals, or any combination thereof. A metal compound may also comprise a nanocluster, nanoparticle, or other nanoform of pure metal, as well as metal compounds with other elements. Metal compounds may also comprise one or more metal cations and one or more anions. The metals in metal compounds may be in any possible oxidation state.

The term "metal" refers to elements classified on the Periodic Table of the Elements as "transition metals" or as "main group metals". Transition metals also include elements classified as lanthanides and actinides. Main group metals include the elements aluminum, gallium, indium, tin, thallium, lead, bismuth, and polonium. For reference, the inside cover of the text "Organic Chemistry" by Brown and Foote ((2002), Thompson Learning Inc.) denotes which elements belong to which groups in the Periodic Table of the Elements.

Examples of metal compounds include salts and oxides of metals. The term "metal salt" refers to a compound comprising a metal cation and an anion. Metal oxides are compounds comprising a metal cation combined with oxygen. The term "metal salt" also includes mixed oxides, acids, alkoxides, amides, azides, borates, borides, carbides, carboxylates, carbonates, clays, clusters, cyanides, halides, hydroxides, hydrates, hydrides, imides, isocyanides, nitrates, nitrides, phosphides, phosphates, sulfides, sulfates, silicates, silicides, superacids, thiocyanate, and thiolates of metals.

An extensive range of metal compounds may be dissolved in ionic liquids to form ionic liquid catalysts. Salts and oxides of transition metals, including platinum, palladium, iridium, rhodium, ruthenium, rhenium, gold, silver, mercury, chromium, molybdenum, tungsten, titanium, zirconium, iron, manganese, technetium, osmium, copper, vanadium, niobium, tantalum, and cobalt, as well as the lanthanide and actinide series of the Periodic Table of the elements, may be useful in the production of ionic liquid catalysts.

Specific salts and oxides of metals that may be dissolved in ionic liquids to produce ionic liquid catalysts include $PtCl_2$, $PtC_4$, $PtO_2$, $PdCl_2$, $RuCl_3$, $RhCl_3$, $IrCl_4$, $AuCl_3$, $Fe_2O_3$, $V_2O_5$, $MnO_2$, $CuCl_2$, $CuCl$, $MgSO_4$, $OSCl_3$, $AlCl_3$, and $FeCl_3$.

A skilled artisan would recognize that there are many other metal compounds that may be used in the system that are readily identifiable without undue experimentation.

As used herein, the term "high-pressure reactor" refers to a reactor system that has greater than atmospheric pressure (around 14.7 psi). In the case of reactions involving methane, high pressure reactors may have added methane gas that increases the pressure of the system. Additional gases may also be used to pressurize a reaction system.

The reaction systems disclosed herein reference a reaction system described by Periana et al. (Periana R. A. et al., (1998) *Science* 280:560-564). One of the catalysts disclosed in this publication, dichloro(η-2-{2,2'-bipyrimidyl})platinum(II), (abbreviated as [bpym]PtCl$_2$) is a produced by Catalytica Advanced Technologies Inc. of Mountain View Calif. This compound may be referred to as the "Periana" catalyst or the "Catalytica" catalyst herein.

Room-temperature ionic liquids are believed to be an excellent replacement for volatile organic solvents, concentrated acids, and concentrated basic solutions that are undesirable due to environmental concerns. In addition, they may dissolve compounds that are not readily soluble in aqueous or organic solvent systems. Ionic liquids have been used as clean solvents and catalysts for green chemistry and as electrolytes for batteries, photochemistry and electrosynthesis. They have no significant vapor pressure and thus create no volatile organic contaminants. They also allow for easy separation of organic molecules by direct distillation without loss of the ionic liquid. Their liquid range can be as large as 3,000° C.

allowing for large reaction kinetic control, which, coupled with their good solvent properties, allows small reactor volumes to be used.

By changing the anion or the alkyl chain on the cation of an ionic liquid, a number of properties, such as hydrophobicity, viscosity, density, and solvation may be varied. For example, ionic liquids may dissolve a wide range of organic molecules to an appreciable extent, the solubility being influenced by the nature of the counter anion.

Another beneficial feature of ionic liquids is their designability: miscibility with water or organic solvents can be tuned through sidechain lengths on the cation and choice of anion. Furthermore, they can be functionalized to act as acids, bases or ligands.

Due to the capacity for ionic liquids to serve as acids, bases, coordination ligands, and nucleophiles, it is possible that ionic liquids themselves catalyze chemical reactions as well as solubilizing reaction components. It is known that several types of chemical reactions, such as Diels-Alder reactions and Friedel-Crafts reactions, occur in ionic liquids.

Metals have been shown to be involved in a large number of chemical reactions. In many cases, they are used as catalysts or cofactors to promote chemical reactions that would otherwise not occur under desirable reaction conditions. However, many of these catalytically-useful metals are insoluble in aqueous or organic reaction systems, leading to their use as heterogeneous catalysts. Heterogeneous catalysts are often rate-limited by the rate of diffusion of reactants and products to and from the metal surface. As a result, homogeneous catalytic systems are generally more efficient.

Ionic liquids may provide a more efficient catalytic system due to their ability to dissolve many metal compounds that would not normally be soluble in other solvent systems. In some embodiments of the invention, ionic liquids that have a melting point between −100° C. and 300° C. may be used. Further embodiments provide for ionic liquids that have a melting point between 30° C. and 300° C. Ionic liquids containing dissolved metals are referred to as "ionic liquid catalysts" and may catalyze a wide variety of different types of chemical reactions, including but not limited to oxidations, substitutions, isomerizations, additions, C—H bond activations, C—N bond activations, C—C bond activations, hydrogenations, dehydrogenations, alkylations, acylations, nucleophilic displacement reactions, and radical reactions.

Ionic liquids may be used as ligands for metal catalysts, whereby the catalytic metal center may be directly attached to the reaction media through coordination, rather than simply being dissolved in it. Because metals may be mobilized on ionic liquids, ionic liquids also provide a means to regenerate or recycle the metals. Additionally, catalytic systems comprising metals dissolved in ionic liquids containing larger organic side chains may mimic the catalytic behavior of macromolecules such as proteins or nucleic acids.

Ionic liquid catalysts are generally produced by dissolving a metal compound in an ionic liquid. While many ionic liquid catalysts are generally homogeneous catalysts that enable chemical reactions to occur without rate-limiting steps associated with diffusion of reactants and products to and from solid surfaces, it is also possible for ionic liquid catalysts to comprise metal catalysts in a solid state, such as in a slurry. Dissolution of metal compounds in ionic liquids may occur at a variety of different temperatures, and some embodiments of the invention provide methods wherein dissolution generally occurs between about 15° C. and about 350° C. The molar ratio of the amount of ionic liquid to the amount of metal compound in the ionic liquid catalyst may range from about 1,000,000:1 to about 1:1. Dissolution of ionic liquid catalysts, as well as reactions catalyzed out in the presence of ionic liquid catalysts may be carried out under a range of different pressures. Certain embodiments of the invention provide for reaction systems wherein the pressure is between around 1 and around 1,500 psi.

Likewise, catalytic reactions involving ionic liquid catalysts may occur at a variety of different temperatures. In certain embodiments of the invention, chemical reactions are carried out in systems between about 25° C. and about 350° C.

A skilled artisan would recognize that there are a number of deletions, substitutions, and modifications of the ionic liquids in the ionic liquid catalysts that would achieve satisfactory dissolution of desired metal compounds that may be identified without undue experimentation.

Reaction systems involving ionic liquid catalysts may be carried out under a variety of different pressures. In certain embodiments of the invention, chemical reactions may be carried out at ambient pressures, which range from about 14.7 psi to about 300 psi. In embodiments where a high-pressure system is used, such as one involving a gas-phase reactant, system pressures may range from around 200 psi to around 5,000 psi.

Certain embodiments of the invention relate to methods wherein solutions comprising ionic salts and salts of platinum are contacted with methane in the presence of concentrated $H_2SO_4$, which may range from 1 to 99 percent by weight. Such reactions generally catalyze the oxidation of methane by the activation of a single C—H methane bond. Platinum is a powerful oxidant; depending on the ligands present, platinum may oxidize methane all the way to carbon dioxide ($CO_2$). One of the benefits of the catalytic system disclosed herein is that the ionic liquid may provide a coordination environment for the platinum that allows for the oxidation of a single C—H bond to produce methanol rather than a complete oxidation of methane to $CO_2$.

Examples of platinum salts and oxides that are useful for these particular embodiments include $PtCl_2$, $PtCl_4$, and $PtO_2$. These metal compounds are relatively insoluble in concentrated $H_2SO_4$ alone, but are readily dissolved in imidazolium and pyridinium-based ionic liquids with chloride or bisulfate as the anion. Heat may be used to promote the dissolution process. In some embodiments of the invention, the reaction occurs between about 150° C. and about 220° C.

Methane may be introduced into the system by a variety of mechanisms, including pressurization of the reaction vessel with methane in a high-pressure reactor, or by bubbling methane through the reaction solution. The reaction vessel for this particular reaction as well as other reactions involving ionic liquid catalysts may be sealed or open to the atmosphere.

The initial product between methane and ionic liquid catalysts in the presence of concentrated $H_2SO_4$ is usually methyl bisulfate. Methyl bisulfate may be converted to methanol by a number of methods that are well-known in the art.

Some embodiments of the invention use ionic liquid catalysts wherein the cationic portions of the liquid comprise alkyl or heteroatom substituents. Certain embodiments provide for reaction systems wherein the cationic portion is unreactive towards the dissolved metal agents, for example, ionic liquids IL-003 through IL-009 shown in Table 1.

The anionic component of an ionic liquid may comprise a number of different negatively-charged compounds. Often, the solubility and reactivity of ionic liquid catalysts may be mediated by its anionic component. Examples of ionic liquid anions that may be suitable for reactions involving the oxidation of methane include but are by no means limited to chloride, bromide, iodide, bisulfate, triflate, and methanesulfate.

In some embodiments of the invention, imidazolium-based ionic liquid systems may demonstrate greater reactivity than the Catalytica catalyst system when tested under the same temperature and pressure conditions. The effect of cation structure (i.e., different alkyl group combinations on the imidazolium ring), anion (e.g., $Cl^-$ vs. $HSO_4^-$), and Pt species (i.e., $PtCl_2$ vs. $PtCl_4$ vs. $PtO_2$) on the reactivity were systematically investigated and are shown in the Examples.

There are a number of other metals that can be dissolved in ionic liquids to yield catalytically-useful, homogeneous and heterogeneous organometallic solutions. Other embodiments of the invention relate to the use of ionic liquid catalysts comprising an ionic liquid and a dissolved iridium (Ir) salt to catalyze the alkylation of benzene.

Ionic liquids provide many possibilities to form catalytic solutions with metal compounds. Therefore, additional embodiments provide for ionic liquid catalysts to be used for combinatorial and high-throughput screening applications.

For chemical reactions using an ionic liquid catalyst, additional substances may be added to the ionic liquid solution. Examples of other substances that may be added to ionic liquid catalyst solutions include but are not limited to water or aqueous solutions, organic solutions, organic or inorganic salts, metals, or other organic or inorganic compounds.

All patents, patent publications, provisional applications and publications referred to or cited herein are incorporated by reference in their entirety, including all figures and tables, to the extent that they are not inconsistent with the explicit teachings in this specification.

It should be understood that the examples and embodiments described herein are for illustrative purposes only and that various modifications or changes in light thereof will be suggested to persons skilled in the art and are to be included within the spirit and purview of this application.

EXAMPLES

Example 1

Compatibility of Oxidants and Reactants in Ionic Liquid Catalytic Systems

Tests were performed to determine the stability of oxidants and reactants for the conversion of methane to methanol, a process that requires $H_2SO_4$. Previous studies tested the compatibility for binary systems of ionic liquid—$H_2SO_4$ and the Periana catalyst, [bpym]$PtCl_2$—$H_2SO_4$, at room temperature and at elevated temperatures (up to 220° C.). A binary system refers to a reaction system with two components. This example describes compatibility tests for two binary systems that include new varieties of ionic liquids as well as other types of Pt-based catalysts. Solubility tests of Pt-based catalysts in ionic liquids were also conducted.

The solubility and stability of four types of ionic liquids (ammonium-based, phosphonium-based, pyridinium-based, and imidazolium-based) in $H_2SO_4$ were analyzed as shown in Table 2. The cation and anion of each ionic liquid were separately evaluated for their stability in $H_2SO_4$. In some cases, the anions were released in the form of HX gas (X=$Cl^-$ or $Br^-$). It was also observed that the ionic liquid [bmim][$BF_4$] was stable at elevated temperatures based on $^1H$ NMR observations, but the anion ($BF_4^-$) decomposed to HF and $BF_3$ in $H_2SO_4$. As shown in Table 2, upon heating all cations stay stable but all anions except triflate ($CF_3SO_3^-$) decompose in $H_2SO_4$. It is possible that a more stable anion, bisulfate ($HSO_4^-$), may form after the decomposition.

TABLE 2

Compatibility between ionic liquids and concentrated sulfuric acid at room temperature (RT) and at elevated temperatures.

| Ionic Liquid | Solubility in $H_2SO_4$ at RT | Stability in $H_2SO_4$ up to 200° C. Cation | Anion |
|---|---|---|---|
| Ammonium-based | | | |
| $(CH_3)_3N(C_{14}H_{29})Br$ | Soluble | Stable | HBr released |
| $(CH_3)_4NCl$ | Soluble | Stable | HCl released |
| Phosphonium-based | | | |
| $(CH_3)_3P(C_{16}H_{33})Br$ | Soluble | Stable | HBr released |
| Pyridinium-based | | | |
| [bpy][Cl] | Soluble | Stable | HCl released |
| Imidazolium-based | | | |
| [bmim][$PF_6$] | Slow and small | | |
| [mmim][$CH_3SO_4$] | Soluble | Stable | Decomposes |
| [bmim][Cl] | Soluble | Stable | HCl released |
| [bmim][$BF_4$] | Soluble | Stable | HF/$BF_3$ released |
| [emim][$CF_3SO_3$] | Soluble | Stable | Stable |
| IL-001 (chloride) | Soluble | Stable | HCl released |
| IL-002 (bromide) | Soluble | Stable | HBr released |

It has been shown previously that the Catalytica catalyst ([bpym]$PtCl_2$) dissolves well and is stable in concentrated sulfuric acid at room temperature (Periana R. A. et al., (1998) *Science* 280:560-564). Several other Pt-based compounds including [$NH_3]_2PtCl_2$, $K_2PtCl_4$ and $PtCl_2$ were added to measure solubility and stability. For example, [$NH_3]_2PtCl_2$ shows better catalytic activity at 180° C. than [bpym]$PtCl_2$. $PtCl_2$ is the product after the decomposition of [$NH_3]_2PtCl_2$ and is insoluble in $H_2SO_4$, and $K_2PtCl_4$ is the starting material for the synthesis of [bpym]$PtCl_2$ (Periana R. A. et al., (1998) *Science* 280:560-564). The compatibility study of these four types of Pt-based compounds is presented in Table 3. The free ligand, bipyrimidine (bpym), was visible after [bpym]$PtCl_2$ was heated at elevated temperatures, but no $PtCl_2$ precipitated.

TABLE 3

Compatibility of Pt-based catalysts in concentrated sulfuric acid at room temperature and at elevated temperatures.

| Pt-based Catalyst | Solubility and Stability in $H_2SO_4$ Room Temp. | High Temp., up to 220° C. |
|---|---|---|
| [bpym]$PtCl_2$ | Yes | Free ligand bpym is observed by NMR at >110° C. |
| [$NH_3]_2PtCl_2$ | Yes | Decomposes at >180° C. and $PtCl_2$ precipitates. |
| $K_2PtCl_4$ | No, decomposes to $PtCl_2$ | No |
| $PtCl_2$ | No | No |

Ionic liquids themselves are often powerful solvents. The solubility of Pt-based catalysts in a variety of imidazolium-based ionic liquids was tested. The molar ratio of ionic liquid to Pt-compound was at least 4:1 to promote a complete dissolution if applicable. As shown in Table 4, the dissolution is greatly facilitated with heating and may depend on the anion.

Chloride and bisulfate ionic liquids readily dissolve all Pt-based catalysts after heating at 200° C. The cations, such as [bmim] and [emim], did not seem to significantly affect the solubility.

Figure 2:
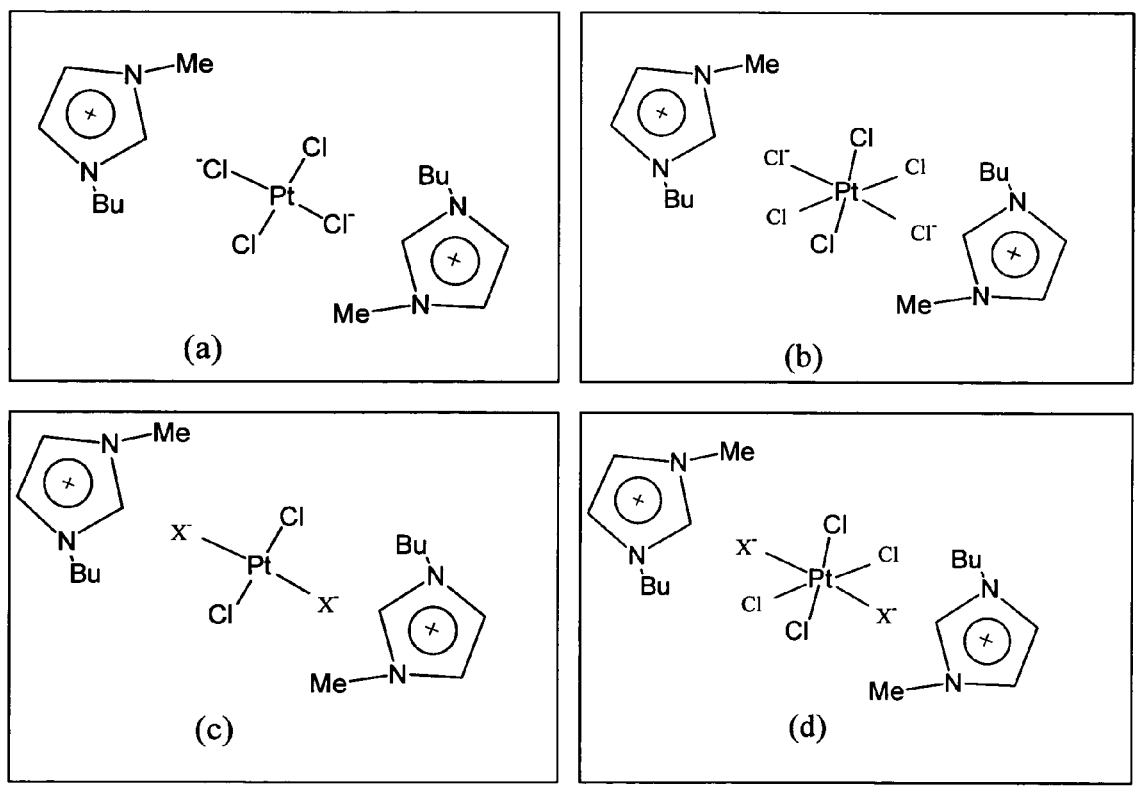
FIG. 2 shows various structures for $PtCl_2$ dissolved in [bmim][X](X=Cl⁻ or $HSO_4^-$) at 200° C. in air in accordance with an embodiment of the present invention.

Since dialkylimidazolium choloroplatinates (both II and IV) have been synthesized under similar conditions (Hasan, M. et al., (2001) *Inorg Chem* 40:795-800), it has been proposed that the dissolution during heating may be a chelating process in which the anions of the ionic liquid coordinate to the Pt center to form a new anion. Using $PtCl_2$ in [bmim][Cl] as an example, a new structure is illustrated in FIG. 2(*a*). The new compound (with excess ionic liquid) is soluble in concentrated $H_2SO_4$, presumably due to the replacement of $Cl^-$ by $HSO_4^-$ (FIG. 2 (*c*)). It is possible that $PtCl_2$ may be oxidized to Pt(IV) during heating, and two additional new structures associated with Pt(IV) are shown in FIGS. 2(*b*) and (*d*).

TABLE 4

Compatibility of Pt-based catalysts in ionic liquids, primarily dependent on the type of anion.

| Ionic Liquid | Pt-based Catalyst Solubility in IL, up to 220° C. | | | |
|---|---|---|---|---|
| | [bpym]PtCl$_2$ | [NH$_3$]$_2$PtCl$_2$ | K$_2$PtCl$_4$ | PtCl$_2$ |
| [bmim][BF$_4$] | No | No | No | No |
| [emim][CF$_3$SO$_3$] | No | No | No | No |
| [bmim][Cl] | Yes at 200° C.; free bpym is seen | Yes upon melting | Yes at 200° C. | Yes upon melting |
| [bmim][HSO$_4$] | Yes at 200° C.; free bpym is seen | Yes at 200° C. | Yes at 200° C. | Yes at 200° C. |

After studies of binary systems, ternary systems at elevated temperatures were tested for stability. The catalyst [bpym]PtCl$_2$ was used as the primary catalyst, but PtCl$_2$ and K$_2$PtCl$_4$ were also studied for comparison. The results are summarized in Table 5. Commercially available ionic liquids usually have dialkyl groups on the imidazolium ring. Table 5 shows that alkyl groups longer than methyl may not be stable in the presence of Pt-based catalysts in heated sulfinuric acid.

It was found that K$_2$PtCl$_4$ and PtCl$_2$ had similar catalytic capability when dissolved in ionic liquids. Furthermore, seven new ionic liquids (IL-003 to IL-009; shown in Table 1) have been designed and synthesized in our laboratory in order to develop a stable ternary system for methane oxidation rather than oxidizing the ionic liquid itself.

TABLE 5

Stability of ternary systems of H$_2$SO$_4$/Catalyst/Ionic Liquid at 200° C.

| Ionic Liquid | Pt-based Catalyst[a] | | |
|---|---|---|---|
| | [bpym]PtCl$_2$ system | K$_2$PtCl$_4$ system | PtCl$_2$ system |
| [mmim][CH$_3$SO$_4$] | Cation stable; Anion decomposed | (Insoluble) | (Insoluble) |
| [emim][CF$_3$SO$_3$] | Ethyl oxidized; Anion stable | (Insoluble) | (Insoluble) |
| [bmim][BF$_4$] | Butyl oxidized; BF$_4$ decomposed | (Insoluble) | (Insoluble) |
| [bmim][Cl]/[HSO$_4$] | Butyl oxidized | Butyl oxidized | Butyl oxidized |
| IL-003 to IL-009[b] | Compatible | Compatible | Compatible |

[a]Pt-based catalysts were either dissolved in H$_2$SO$_4$ first or in ionic liquid first at elevated temperature.
[b]Ionic liquids (IL-003 to IL-009) are home designed and synthesized and meet the compatibility requirement in the ternary system up to 220° C.

Example 2

Conversion of Methyl Bisulfate to Methanol

The majority of the ionic liquids that have been tested have been shown to be miscible with methanol (CH$_3$OH) and are generally stable. Deuterated methanol (CD$_3$OD) may be a good NMR solvent for ionic liquids. A small amount of methanol in concentrated sulfuric acid may exist in the form of methyl bisulfate (CH$_3$HSO$_4$), as evidenced by $^1$H NMR using D$_2$SO$_4$ as a solvent.

Extraction of methanol from concentrated sulfuric acid after the methane oxidation reaction may be one of the steps in the methane conversion process. The hydrolysis and neutralization of a standard methyl bisulfate solution in sulfuric acid was measured to model the process following oxidation of methane. About 55.7 μL CH$_3$OH was dissolved in 10 mL 96% H$_2$SO$_4$. From this solution, 0.2 mL was removed and hydrolyzed into 5 mL deionized water to give a formal 100 ppm solution. Sodium hydroxide was added into the water solution to reach pH=7, which is a desirable condition for GC-MS (gas chromatography mass spectrometry) measurement. Neutralization was conducted in an ice bath with magnetic stirring to prevent methanol loss. GC-MS produced two peaks that could be assigned to methanol; one representing the free CH$_3$OH and the other for the remaining CH$_3$HSO$_4$. This indicates that the hydrolyzation is incomplete in 5 mL of water solution. A direct 100 ppm methanol solution in water was prepared and subjected to GC-MS measurement under the same conditions. The methanol peak position matched one of the two peaks from the neutralized solution. However, the peak area (100 ppm) was larger than the two peaks combined in the latter case, implying hydrolysis and titration lead to some loss of methanol.

Example 3

Ambient Pressure Reactor Tests for Alkyl Oxidation

Studies using a low-pressure reactor were carried out to observe the kinetics of methane activation. Because the solubility of methane gas in sulfinuric acid solution at low pressures is somewhat low, the hydrogen/deuterium exchange rate in D$_2$SO$_4$ may be very small. An alternative method was used to model the effect of platinum-containing ionic liquid catalysts on a hydrocarbon moiety. Since 1-methyl-3-butyl-imidazolium chloride ([bmim] [Cl]) may dissolve all types of Pt-based catalysts (Table 4) and the butyl group may be oxidized in a ternary system (Table 5), it can be used instead of methane as a model compound for oxidation rate study. A systematic comparison between three catalytic systems, i.e., [bpym]PtCl$_2$, K$_2$PtCl$_4$, and PtCl$_2$, is presented in Table 6.

TABLE 6

Oxidation rate study of H$_2$SO$_4$/Catalyst/[bmim][Cl] ternary system at 200° C. [bmim] was used as a model compound for oxidation. Rates were determined based on $^1$H NMR in D$_2$SO$_4$ using acetic acid as the external standard.

| Time at 200° C. | [bpym]PtCl$_2$ system | | K$_2$PtCl$_4$ system | | PtCl$_2$ system | |
|---|---|---|---|---|---|---|
| | Conversion[a] | Yield[a] | Conversion | Yield | Conversion | Yield |
| R.T. (ref.) | 0 | 0 | 0 | 0 | 0 | 0 |
| 70 min | 37% | 37% | 47% | 20% | 24% | 12% |
| 2 hr | 65% | 55% | ~60% | 24% | ~40% | 21% |
| 27 hr | 100% | 100% | 80% | 72% | 50% | 50% |

[a]See the definitions of conversion and yield in the text.

Typical experimental conditions were 0.05 mmol Pt-based catalyst and 0.73 mmol ionic liquid in 1 mL 96% H$_2$SO$_4$ at atmospheric pressure using oil bath (200° C.) and magnetic stirring. The rates were all normalized to references that were prepared at room temperature. Only the butyl group on the imidazolium ring was observed to be oxidized and the methyl group was not. The conversion rate is arbitrarily defined from NMR as the intensity decrease of the —CH$_3$ on the butyl group. When the butyl group changes, the electronic environment of the methyl group also changes, which leads to a new —CH$_3$ peak adjacent to the old one. As expected, the total intensity remained nearly the same. The yield rate is thus defined as the amount of the newly-formed —CH$_3$ peak intensity relative to the total.

Figure 3A:
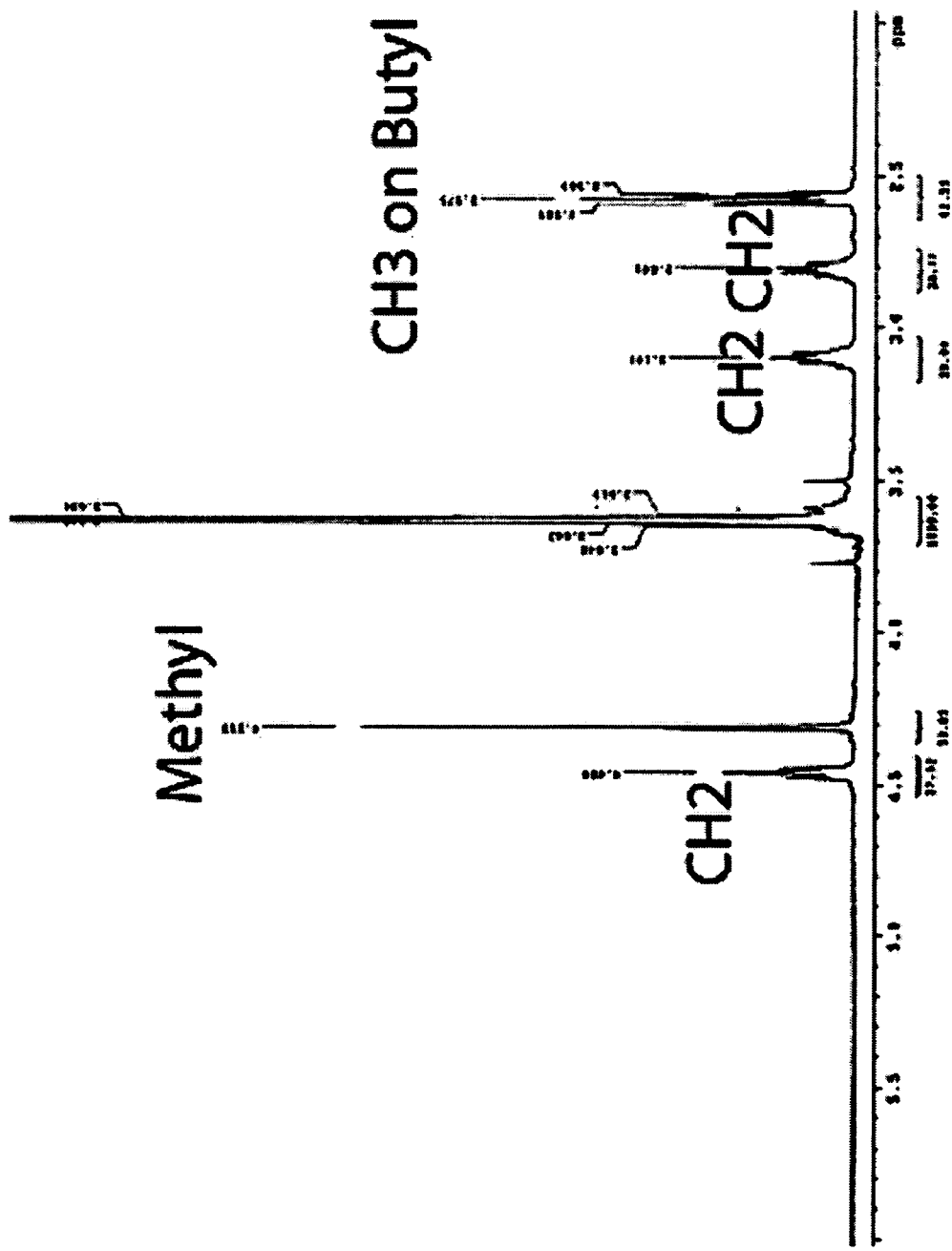
FIG. 3a shows a spectrum at room temperature, as reference.
Figure 3B:
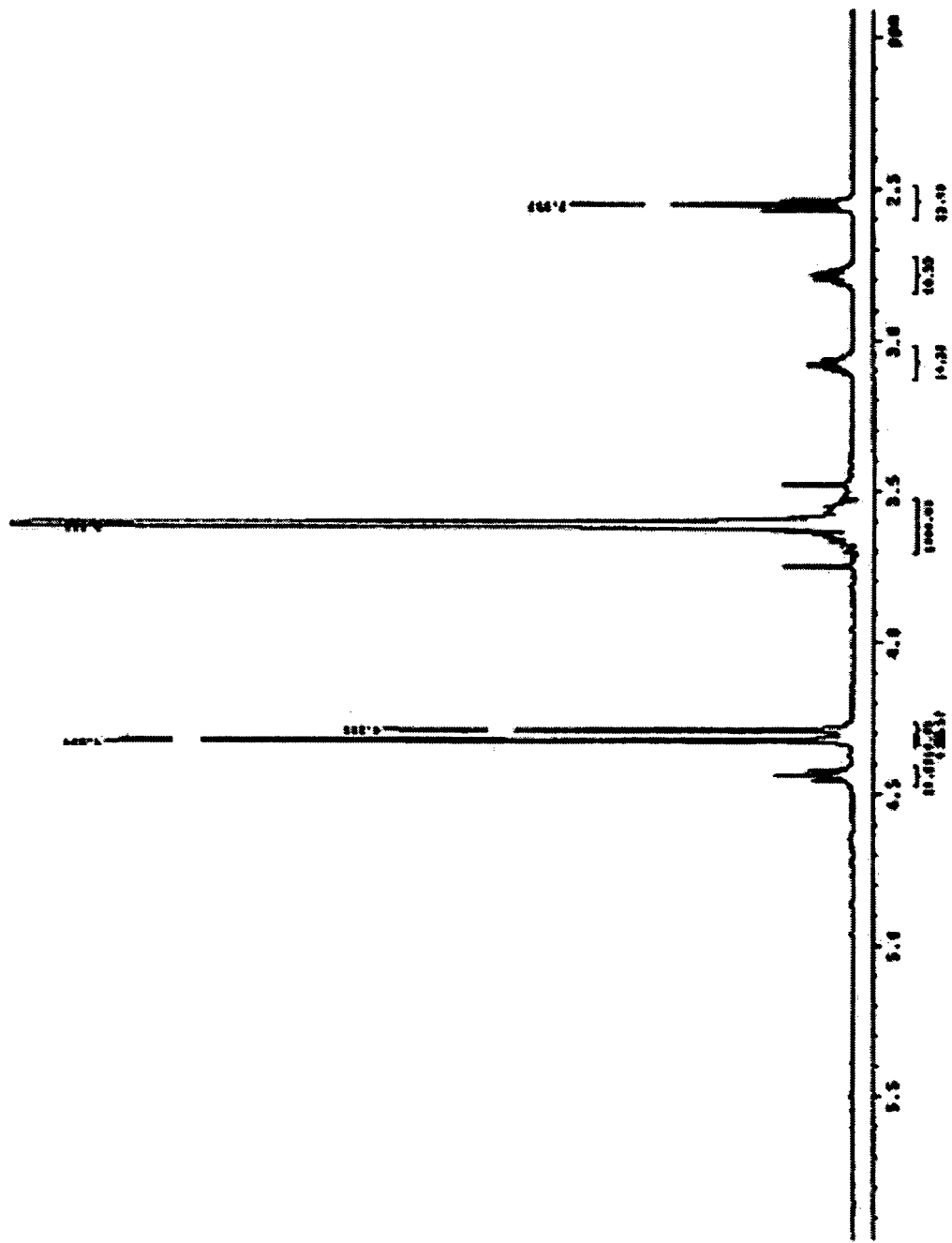
FIG. 3b shows a spectrum at 200° C. at 2 hr.
Figure 3C:
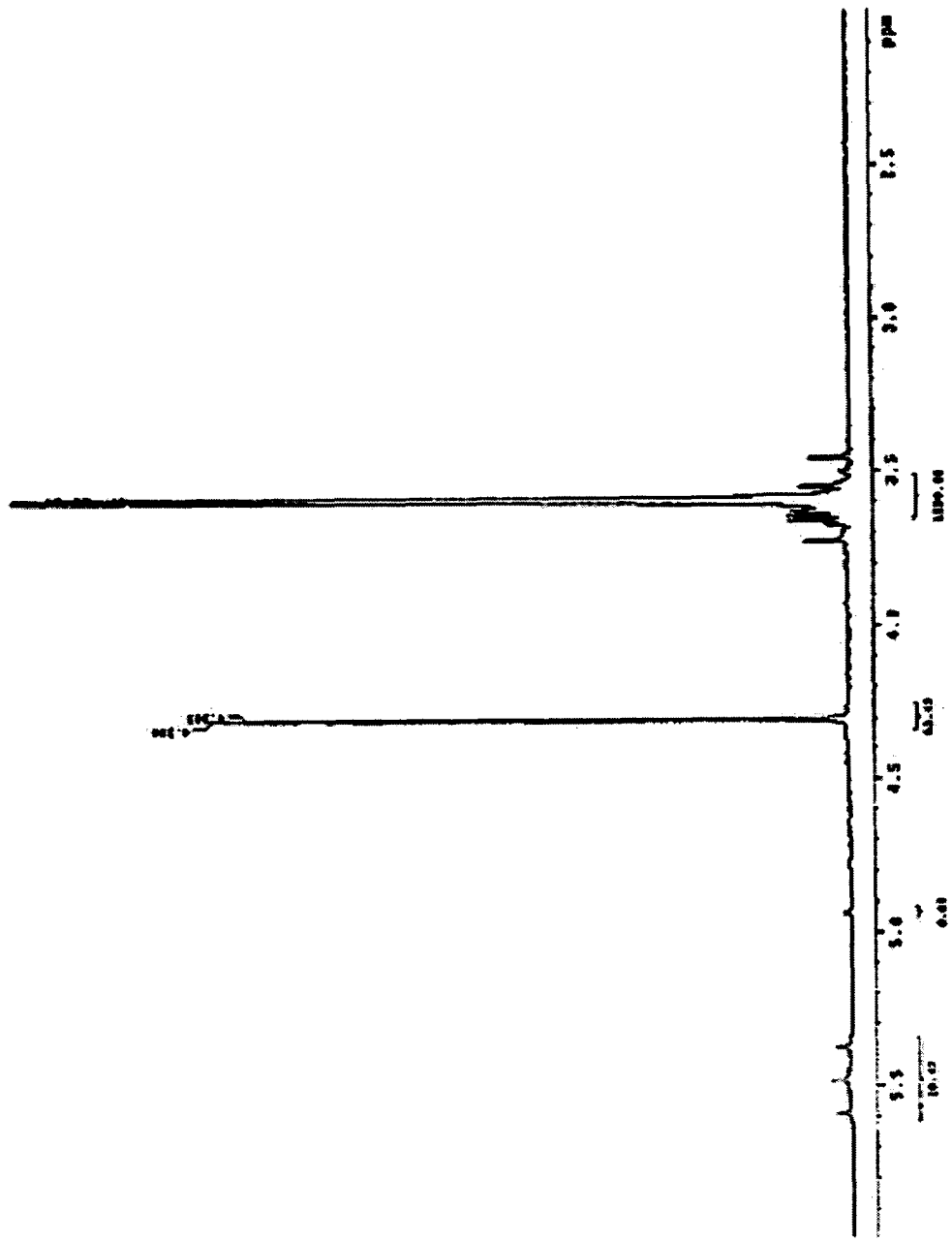
FIG. 3c shows a spectrum at 200° C. at 27 hr.

As seen in Table 6, the oxidation rate was fastest in the [bpym]PtCl$_2$ system and decreases in the order of [bpym]PtCl$_2$, K$_2$PtCl$_4$, and PtCl$_2$. The $^1$H NMR spectra for the [bpym]PtCl$_2$ system reacted for different time were plotted in FIG. 3.

Example 4

Figure 4A:
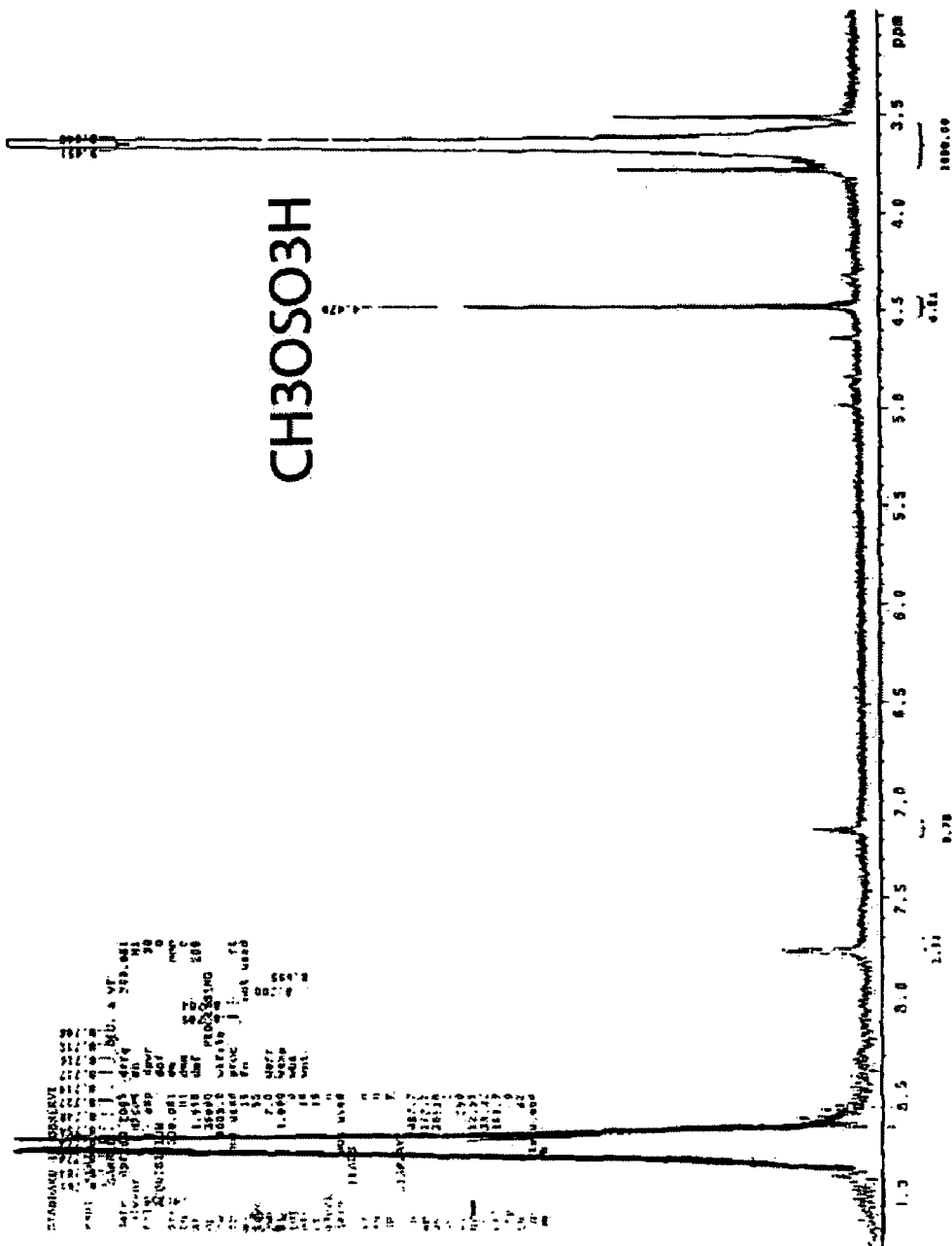
FIG. 4a shows system #1, using [bpym]$PtCl_2$ as the catalyst.
Figure 4B:
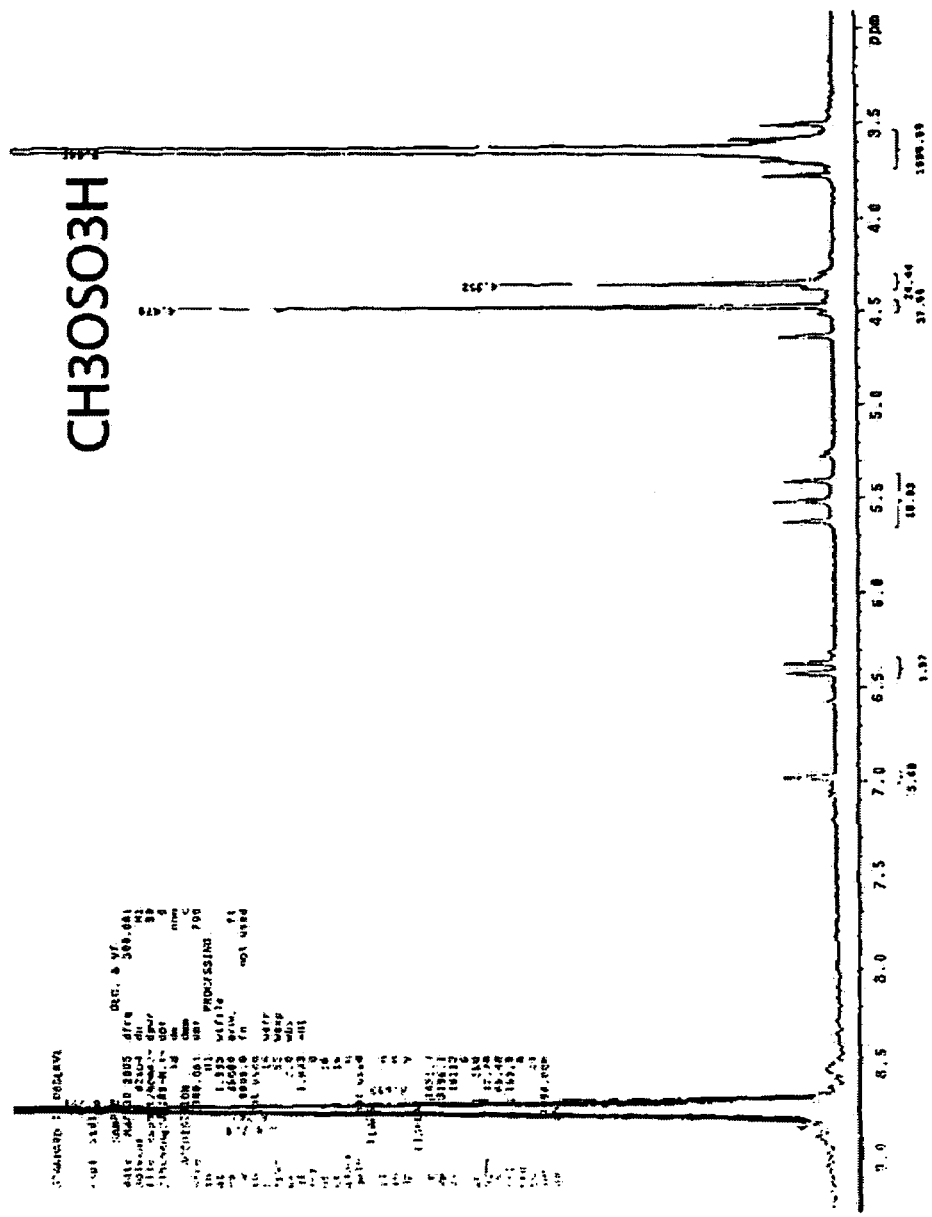
FIG. 4b shows system #2, using $PtCl_2$-IL003 as the catalyst. Acetic acid was used as the external standard.
Figure 5:
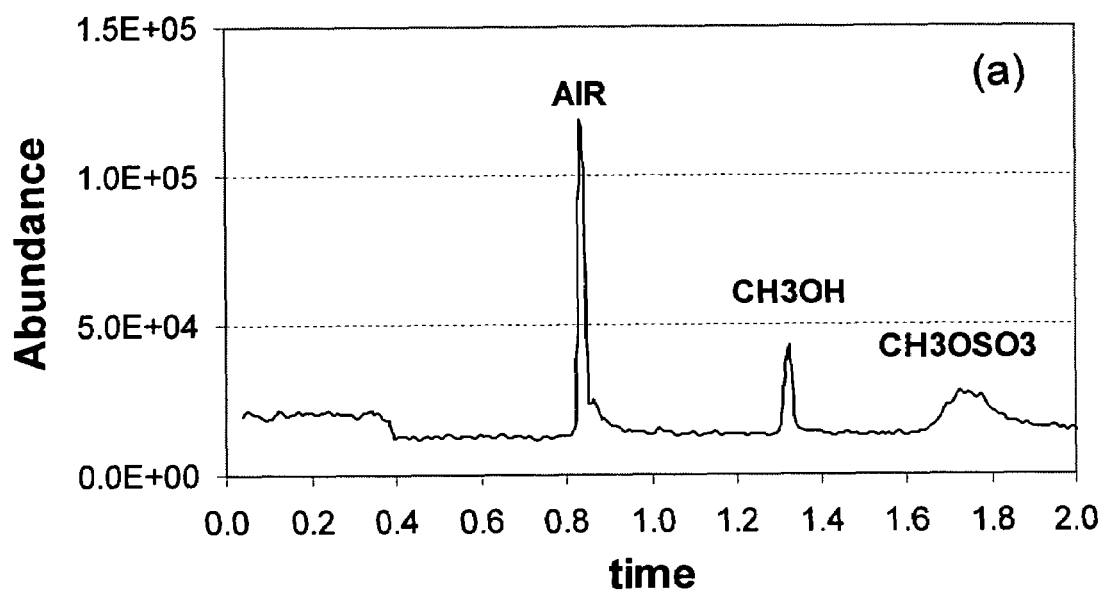
FIG. 5 shows GC-MS spectra of (a) system #1; and (b) system #2 in accordance with an embodiment of the present invention. Following each run, about 0.2 mL liquid was hydrolyzed in 5 mL $H_2O$ solution and then neutralized with NaOH. They differ in the total peak area integrated.
Figure 5:
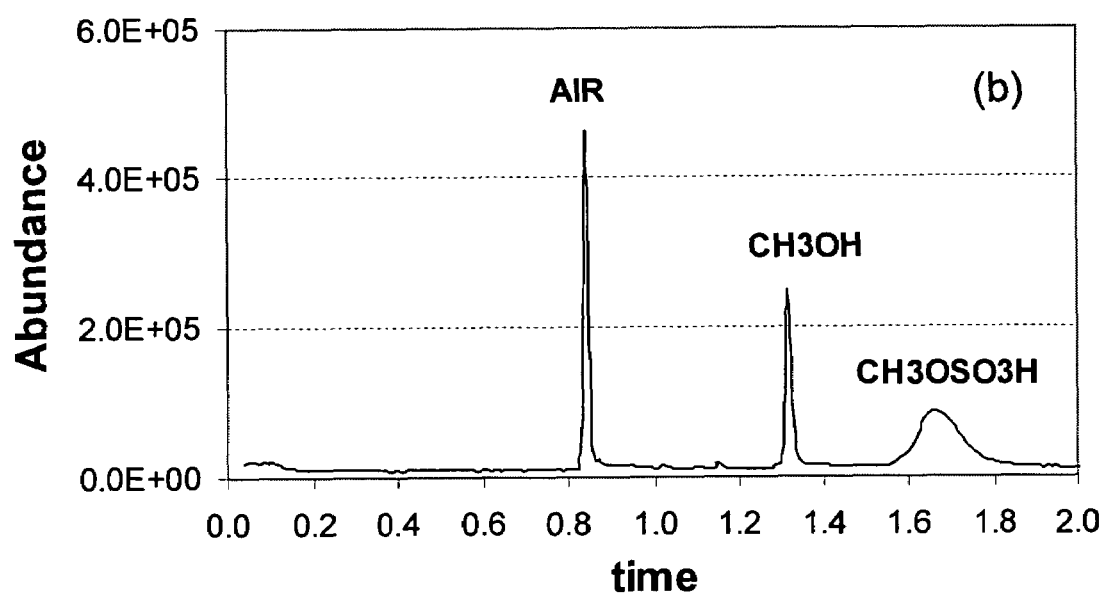

High Pressure Reactor Tests for Methane Oxidation to Methanol Using a Pt(II)-Based Ionic Liquid Catalyst With compatible H$_2$SO$_4$/catalyst/ionic liquid systems developed (Table 5), high pressure reactor tests for direct methane conversion were conducted. About 0.05 mmol of a Pt-based catalyst was dissolved in 0.2 mmol ionic liquid. The resulting ionic liquid catalyst solution was added to 1 mL H$_2$SO$_4$ in a glass tube. The glass tube was sealed in a 61 mL stainless steel reactor that also contains 500 psi high purity methane gas. The reactor was heated at 220° C. in an oil bath with constant magnetic stirring. After 2.5 hours, the reactor was cooled off and gas samples were collected in expansion tubes before the high pressure gas was released. Following the reaction, a sample of the liquid was removed for $^1$H NMR, and another sample was hydrolyzed and neutralized for GC-MS measurements. The sampled gas was subjected to GC analysis. Four systems were tested and the CH$_3$OH yields were reported in Table 7, in which NMR and GC-MS results for each run were consistent. As a comparison between system #1 and #2, their $^1$H NMR spectra are shown in FIG. 4 highlighting the methyl bisulfate peak; and their GC-MS spectra are shown in FIG. 5 highlighting both the free CH$_3$OH peak and the CH$_3$HSO$_4$ peak.

TABLE 7

High pressure reactor tests in Pt-catalyst/H$_2$SO$_4$/Ionic Liquids ternary systems.

| System | CH$_3$OH Yield (relative to system #1) | |
|---|---|---|
| | By $^1$H NMR | By GC-MS |
| System #1 [bpym]PtCl$_2$/H$_2$SO$_4$/CH$_4$ | 1 | 1 |
| System #2 PtCl$_2$-IL003/H$_2$SO$_4$/CH$_4$ | 7 | 5 |
| System #3 PtCl$_2$-IL006/H$_2$SO$_4$/CH$_4$ | 3 | 3.5 |
| System #4 [bpym]PtCl$_2$-IL006/H$_2$SO$_4$/CH$_4$ | 1 | 1 |

System #1 was designed to repeat the experiment conducted by Periana et al., (Periana R. A. et al., (1998) Science 280:560-564) which only differs in reactor design. The previously-published results were used as reference (Table 7). System #2 and #3 used PtCl$_2$-ionic liquid as the catalysts and gave appreciably higher methanol yield (3-5 times more). This demonstrates a great potential of using ionic liquids as a novel media to directly oxidize methane.

System #4 tested the catalytic activity when some ionic liquid was added to system #1 but did not improve any methanol yield. FIG. 4 indicates that CH$_3$HSO$_4$ comprises most of the liquid product from CH$_4$. The triplet peaks between 5 and 6 ppm have not been identified with a specific structure, but parallel experiment without CH$_4$ showed that it originated from the interaction of imidazolium ring and Pt-based catalyst. FIG. 5 indicates the hydrolysis is not complete and both peaks (free CH$_3$OH and CH$_3$HSO$_4$) are counted as the product.

Example 5

High Pressure Reactor Tests for Methane Oxidation to Methanol Using a Pt(IV)-Based Ionic Liquid Catalyst Selected H$_2$SO$_4$/catalyst/ionic liquid ternary systems were tested under several types of conditions. About 0.05 mmol Pt-based catalyst was first dissolved in 03-0.4 mmol ionic liquid and then the total solution was added into 1 mL H$_2$SO$_4$ in a glass tube. The glass tube was sealed in a 69 mL stainless steel reactor that also contains 500 psi high purity methane gas. The reactor was heated at 220° C. in an oil bath with constant magnetic stirring. After 2.5 hours, the reactor was cooled off and gas samples were collected via an expansion volume directly connected to the reactor and finally the remaining high pressure gas was released. Part of the liquid after reaction was taken for $^1$H NMR and part was hydrolyzed and neutralized for GC-MS measurements. The sampled gas was subjected to GC analysis.

Figure 6:
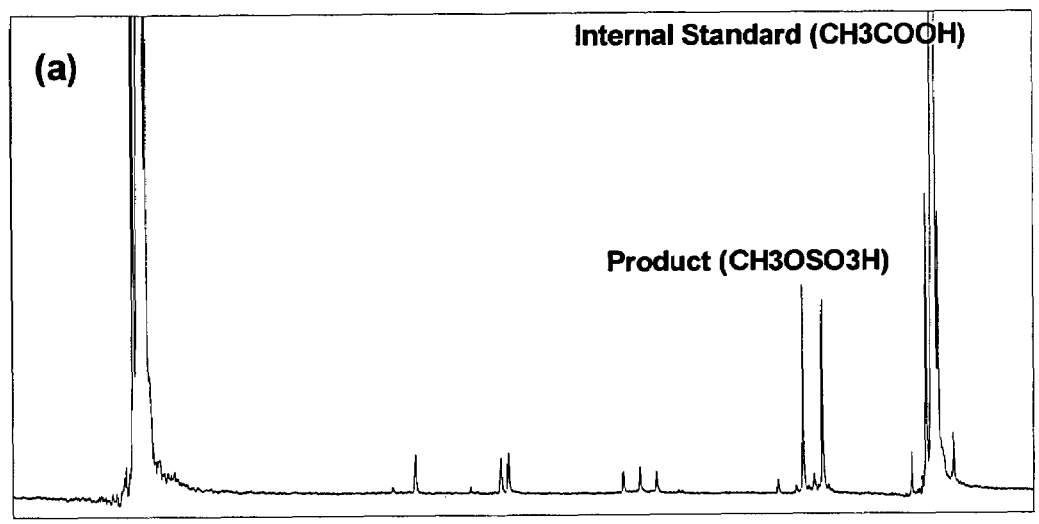
FIG. 6 shows $^1$H NMR spectra of the liquid of $H_2SO_4$/Pt (IV) Catalyst/$CH_4$ ternary system after methane oxidation tests using the high-pressure reactor in accordance with an embodiment of the present invention.
Figure 6:
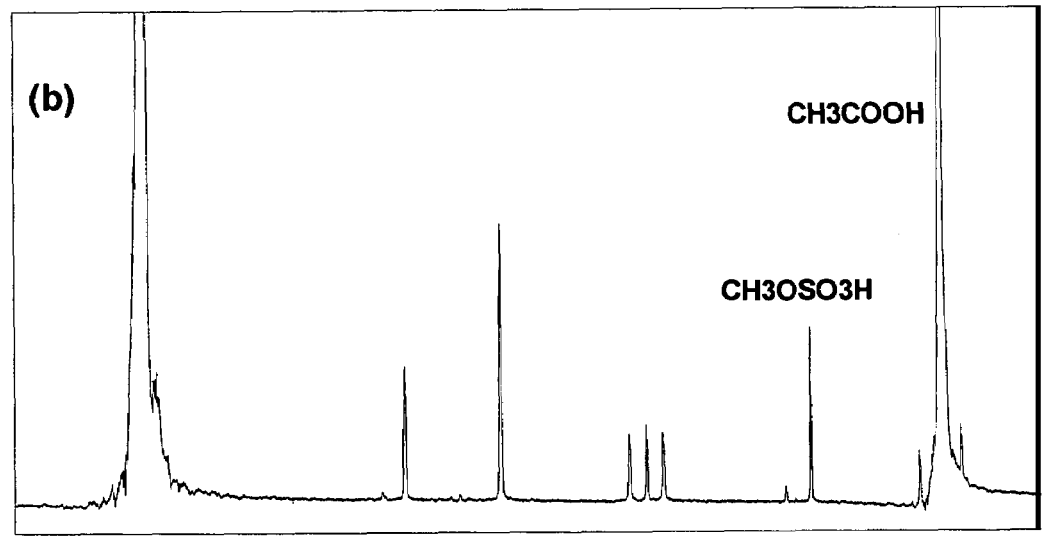

The two $^1$H NMR spectra in FIG. 6 demonstrate that Pt(IV) species in ionic liquids have similar catalytic activity as Pt(II) species reported before. Methylbisulfate (CH$_3$HSO$_4$) is the predominant product from CH$_4$. Both PtC$_4$+IL-003 and PtO$_2$+IL-006 showed a higher methanol yield than the reference reaction, which used the Catalytica [bpym]Cl$_2$ catalyst. While it has been proposed that methane C—H bond activation occurs through a Pt(II) center, the results shown here suggest that Pt(IV) may also activate methane and oxidize it to methanol in sulfuric acid environment.

Figure 7:
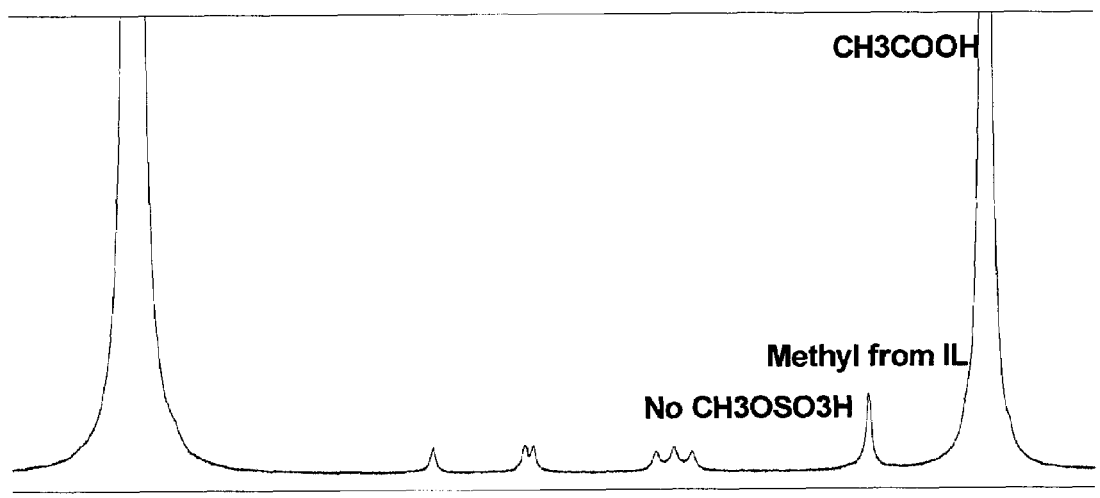
FIG. 7 shows $^1$H NMR spectra from the liquid of methane oxidation test using a non-chlorine-containing system (IL-004/$PtO_2$/$H_2SO_4$) in accordance with an embodiment of the present invention.

It was found that the presence of chlorine in the catalytic system may play a role in catalysis. The methane oxidation test using IL-004 (bisulfate) and $PtO_2$ in sulfuric acid showed no methanol generated (FIG. 7). This contrasts with the results shown in FIG. 2 (b) which also used $PtO_2$ but with a chloride ionic liquid (IL-006). It is possible that the difference may be in the activation energy in these two systems, and that chlorine on Pt sites may help reduce the energy barrier.

Figure 8:
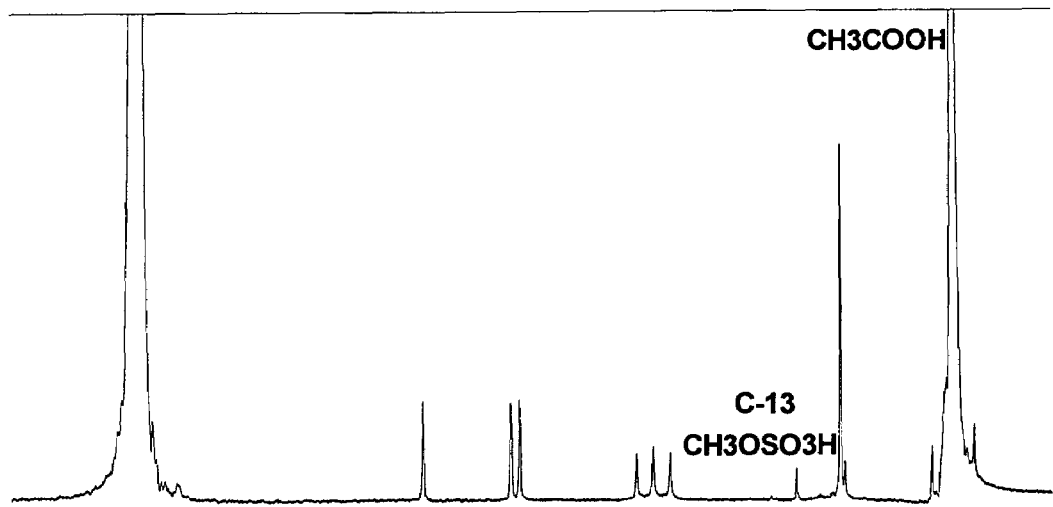
FIG. 8 shows $^1$H NMR spectra from the liquid of Carbon-13 methane oxidation test using $PtCl_2$ and IL-004 in accordance with an embodiment of the present invention.

In some cases, methylated imidazolium-based ionic liquids were used for solvent for platinum catalysts. It is possible that the product methylbisulfate results from the dissociation of the methyl group from the imidazole ring. To test this, an experiment was conducted to test the oxidation of methane using a pure $^{13}CH_4$ as opposed to $^{12}CH_4$ with $PtCl_2$ and IL-004. FIG. 8 shows the majority of methylbisulfate was $13CH_3HSO_4$ (>95%). This suggests that the product is almost exclusively from the oxidation of the methane gas.

Figure 9:
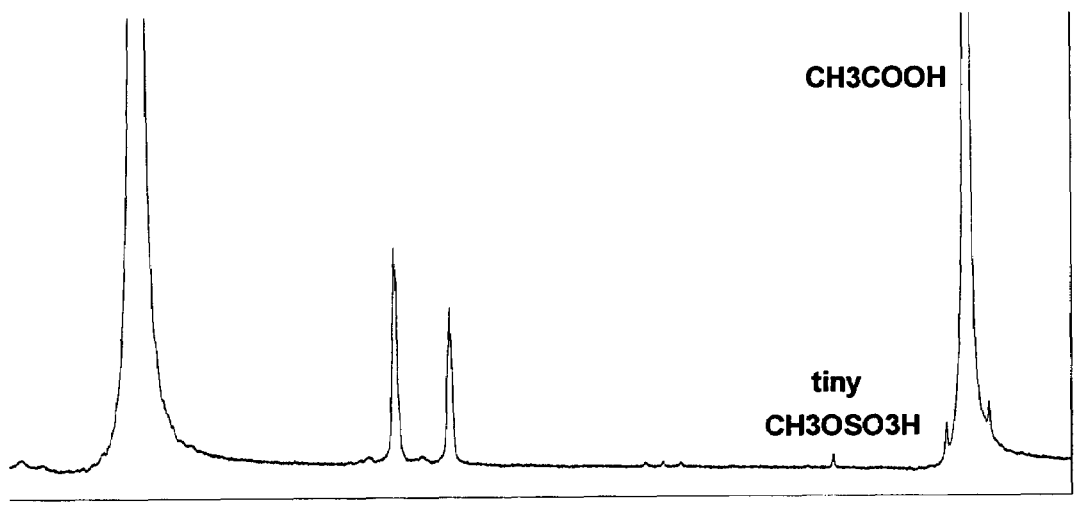
FIG. 9 shows $^1$H NMR spectra from the liquid of methane oxidation test using pyridinium-based IL (IL-020) and $PtCl_2$ in $H_2SO_4$ in accordance with an embodiment of the present invention.

Methane oxidation studies were also conducted using other types of ionic liquids. One example was pyridinium-based ionic liquid (IL-020) and $PtCl_2$. FIG. 9 shows the $^1H$ NMR spectra from the reaction liquid.

An alternative reaction system for methane oxidation studies may be a 1 mL high-pressure gold tube. A gold tube may be loaded with 0.3 mL reaction liquid and 0.7 mL methane gas and then sealed. The sealed tube may be placed in a furnace and external hydraulic pressure up to 1000 psi may be applied. This mini-reactor may sustain uniform heating and pressure and provide a good mass balance. In addition, a commercial 25 mL Parr reactor may be used to provide accurate temperature, pressure, and mass balance control.

What is claimed is:

1. A method of facilitating a homogeneous or heterogeneous catalytic oxidation of at least one C—H bond of a hydrocarbon, comprising:
   providing a quantity of an ionic liquid and a quantity of a metal compound;
   contacting the metal compound with the ionic liquid such that at least a portion of the metal compound dissolves in the ionic liquid to produce an ionic liquid catalyst; and
   using the ionic liquid catalyst to facilitate the homogeneous or heterogeneous catalytic oxidation of the at least one C—H bond of the hydrocarbon, comprising,
   wherein the ionic liquid comprises an imidazolium chloride with any substitution on the imidizole ring and the metal compound comprises platinum.

2. The method of claim 1, wherein the ionic liquid further comprises one or more cationic components and one or more anionic components.

3. The method of claim 2, wherein the cationic component is selected from the group consisting of imidizolium, 1-methylimidizolium, 1,3-dimethylimidizolium, and combinations thereof.

4. The method of claim 2, wherein the anionic component is selected from the group consisting of chloride, bromide, iodide, bisulfate, triflate, trifluoroacetate, methanesulfate, and combinations thereof.

5. The method of claim 1, wherein the ionic liquid is selected from the group consisting of 1-methylimidazolium chloride, 1-methylimidazolium bisulfate, 1-methylimidazolium triflate, imidazolium chloride, imidazolium bisulfate, 1,3-dimethylimidazolium iodide, 1,3-dimethylimidazolium bisulfate, and combinations thereof.

6. The method of claim 1, wherein the ionic liquid has a melting point between about −100° C. and about 300° C.

7. The method of claim 1, wherein the ionic liquid has a melting point between about 30° C. and 300°C.

8. The method of claim 1, wherein the metal compound is selected from the group consisting of $PtCl_2$, $PtCl_4$, $PtO_2$, and combinations thereof.

9. The method of claim 1, wherein the molar ratio of the amount of ionic liquid to the amount of the metal compound is from 1,000,000:1 to 1:1.

10. A method for converting methane into an oxidized product, comprising:
    providing an ionic liquid catalyst; and
    contacting methane gas with the ionic liquid catalyst in the presence of sulfuric acid,
    wherein the ionic liquid catalyst comprises an ionic liquid and a metal compound, the metal compound comprising platinum and the ionic liquid comprising an imidazolium chloride with any substitution on the imidizole ring.

11. The method of claim 10, wherein the ionic liquid is selected from the group consisting of 1-methylimidazolium chloride, 1-methylimidazolium bisulfate, 1-methylimidazolium triflate, imidazolium chloride, imidazolium bisulfate, 1,3-dimethylimidazolium iodide, 1,3-dimethylimidazolium bisulfate, and combinations thereof.

12. The method of claim 10, wherein the ionic liquid has a melting point between about −100° C. and about 300° C.

13. The method of claim 10, wherein the ionic liquid has a melting point between about 30° C. and 300° C.

14. The method of claim 10, wherein the metal compound is selected from the group consisting of $PtCl_2$, $PtCl_4$, $PtO_2$, and combinations thereof.

15. The method of claim 10, wherein the contacting of the methane to the ionic liquid catalyst is by bubbling methane through the ionic liquid catalyst.

16. The method of claim 10, wherein the contacting of the methane to the ionic liquid solution is by pressurizing a reaction system with methane.

17. The method of claim 10, wherein the molar ratio of the amount of ionic liquid to the amount of metal compound is from about 1,000,000:1 to 1:1.

18. The method of claim 10, wherein the oxidized product is methylbisulfate.

19. A method for producing methanol from methane gas, comprising:
    providing an ionic liquid catalyst; and
    contacting methane gas with the ionic liquid catalyst in the presence of sulfuric acid,
    wherein the ionic liquid catalyst comprises an ionic liquid and a metal compound, the metal compound comprising platinum and the ionic liquid comprising an imidazolium chloride with any substitution on the imidizole ring.

* * * * *

UNITED STATES PATENT AND TRADEMARK OFFICE
CERTIFICATE OF CORRECTION

PATENT NO.       : 7,615,644 B2
APPLICATION NO.  : 11/228788
DATED            : November 10, 2009
INVENTOR(S)      : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this

Nineteenth Day of October, 2010

David J. Kappos
*Director of the United States Patent and Trademark Office*